US010660484B1

(12) United States Patent
Okuszka (10) Patent No.: US 10,660,484 B1
(45) Date of Patent: May 26, 2020

(54) SCRUBBING DEVICE

(71) Applicant: ScrubTech LLC, West Long Branch, NJ (US)

(72) Inventor: Joseph Gregory Okuszka, West Long Branch, NJ (US)

(73) Assignee: SCRUBTECH LLC, West Long Branch, NJ (US)

( * ) Notice: Subject to any disclaimer, the term of this patent is extended or adjusted under 35 U.S.C. 154(b) by 243 days.

(21) Appl. No.: 15/911,139

(22) Filed: Mar. 4, 2018

Related U.S. Application Data

(60) Provisional application No. 62/500,664, filed on May 3, 2017.

(51) Int. Cl.
| | |
|---|---|
| *A47K 7/04* | (2006.01) |
| *A61B 90/80* | (2016.01) |
| *A46B 13/04* | (2006.01) |
| *A46B 13/00* | (2006.01) |

(52) U.S. Cl.
CPC .............. *A47K 7/04* (2013.01); *A46B 13/001* (2013.01); *A46B 13/04* (2013.01); *A61B 90/80* (2016.02); *A46B 2200/1006* (2013.01)

(58) Field of Classification Search
CPC .......... A47K 7/04; A47K 3/001; A47K 7/024; A47K 5/1217; A61B 90/80; A61B 2200/1006; A46B 13/04; A46B 11/0017; A46B 13/001
See application file for complete search history.

(56) References Cited

U.S. PATENT DOCUMENTS

| | | | | |
|---|---|---|---|---|
| 727,993 | A | * | 5/1903 | Newport ................ A47K 3/001 4/559 |
| 826,806 | A | | 7/1906 | Scoggins |
| 1,209,041 | A | | 12/1916 | Ruggaber |
| 1,366,306 | A | | 1/1921 | Wick |
| 2,183,051 | A | | 12/1939 | Stuprich |
| 2,345,294 | A | * | 3/1944 | Schauffler ................ A47K 7/04 134/6 |
| 2,723,409 | A | | 11/1955 | Kluba |
| 2,750,610 | A | | 6/1956 | Bloch |
| 2,929,825 | A | | 3/1960 | Stephens et al. |
| 3,439,370 | A | | 4/1969 | McLaughlin |
| 3,576,277 | A | | 4/1971 | Blackmon |
| 3,648,315 | A | | 3/1972 | Hash |
| 3,691,577 | A | | 9/1972 | Bliss |

(Continued)

FOREIGN PATENT DOCUMENTS

DE            2336455 A1 *  2/1975    ........... E03C 1/0408

OTHER PUBLICATIONS

Computer generated English translation of DE 2336455 A1, Mueller, Feb. 1975. (Year: 1975).*

*Primary Examiner* — Laura C Guidotti
(74) *Attorney, Agent, or Firm* — William J. Connelly, III; Maldjian Law Group LLC (57) ABSTRACT

A scrubbing device includes a housing. An axle is rotatably mounted on the housing. The scrubbing device also includes a motor operatively coupled to the axle. The scrubbing device further includes at least one brush wheel and a stone wheel mounted on the axle. The at least one brush wheel includes a plurality of bristles. The scrubbing device also includes a pipe having a plurality of holes disposed above the axle. The pipe is in fluid communication with a source of fluid.

19 Claims, 4 Drawing Sheets

(56) References Cited

U.S. PATENT DOCUMENTS

| | | | |
|---|---|---|---|
| 3,761,989 A | 10/1973 | Gore | |
| 3,918,987 A | 11/1975 | Kopfer | |
| 4,190,919 A | 3/1980 | Burford | |
| 4,295,233 A | 10/1981 | Hinkel et al. | |
| 4,564,968 A | 1/1986 | Buckley | |
| 4,606,085 A | 8/1986 | Davies | |
| 5,199,118 A | 4/1993 | Cole et al. | |
| 5,727,579 A | 3/1998 | Chardack | |
| 5,924,148 A | 7/1999 | Flowers, Sr. | |
| 6,141,811 A | 11/2000 | Nakamura | |
| 6,351,866 B1 | 3/2002 | Bragulla | |
| 6,912,740 B2 * | 7/2005 | Fainberg | A47K 7/026 4/560.1 |
| 8,545,516 B1 * | 10/2013 | Winnett | A61B 17/54 606/131 |
| 8,621,679 B1 * | 1/2014 | Donikian | A47K 7/02 15/21.1 |
| 2011/0038660 A1 | 2/2011 | Rudolph et al. | |

\* cited by examiner

SCRUBBING DEVICE

CROSS-REFERENCE TO RELATED APPLICATIONS

This application claims the benefit of U.S. Provisional Application Ser. No. 62/500,664, filed May 3, 2017, entitled "HAND SCRUBBING DEVICE," which is incorporated herein by reference in its entirety.

FIELD OF THE INVENTION

Embodiments of the present invention generally relate to scrubbing devices, and in particular relate to an electric hand scrubbing device.

BACKGROUND

Good hygienic habits are important for good health. These habits include the need to clean one's body periodically and/or treat one's skin. Further, in the medical field, cleanliness of one's hands is very important to prevent infection to a patient and/or medical staff during and after a surgery. Facilities for washing hands have changed little since the advent of plumbing, consisting primarily of a wash basin and a water source. Further, drying of hands is implemented through the use of disposable paper towels, cloth towels, or hot air hand dryers.

Mechanical scrubbing devices and like devices are often impractical and cumbersome. There is a need for a hand scrubbing device, interchangeably referred to as a scrubbing device that is portable, easy to use and effective at removing dirt and bacteria from hands for better sanitation and health.

SUMMARY

The present invention relates to a scrubbing device, having a water source, controlled by a power device, such as an electric motor, which can be mounted above a sink, wash basin or in a shower.

Embodiments in accordance with the present invention further provide a hand scrubbing device with axially mounted rotating scrub brushes and pumice wheels. More specifically, a user places his/her hands in contact with the scrub brushes and pumice wheel, and manipulates the position of his/her hands in for the desired level of cleaning. The hand scrubbing device is further portable and contained within a housing such as an aluminum or plastic housing. The housing further comprises an inlet pipe that supplies water for cleaning and an overspray shield to blunt water spray coming off the wheels and out of the device. Water is supplied to the inlet pipe from a reservoir or a faucet and dispensed to enable cleaning using the axially mounted rotating scrub brushes and pumice wheels. In another embodiment of the present invention, the hand scrubbing device further comprises a valve to regulate the flow of fluid through the pipe and thereby controlling the amount and rate that fluid is dispensed from the pipe.

Further embodiments of the hand scrubbing device comprise the axially mounted rotating scrub brushes and pumice wheels being coupled to an electric motor. The electric motor may be powered by a rechargeable battery pack. The electric motor provides variable speed control to the axially mounted brushes and pumice wheels. The speed of the electric motor may be calibrated to avoid physical injuries to the hands being cleaned. Alternately, the electric motor may be powered with a power cord plugged into an electrical outlet. The housing further comprises a control unit with sensors that detect the presence of a user wherein the hand scrubbing device may be automatically activated or de-activated. The hand scrubbing device may also be automatically de-activated upon sensing pressure, which is higher than a threshold limit, from a user's hand on the axially mounted brushes and pumice wheel.

In yet other embodiments of the present invention, the hand scrubbing device may be coupled to a reservoir tank from which water is supplied. The reservoir tank may be filled manually or from a pipe connected to a faucet. Alternately, the hand scrubbing device may be supplied with water directly from the faucet through a pipe connecting the faucet and the housing of the hand scrubbing device. The hand scrubbing device may further comprise a valve to regulate the flow of fluid from the fluid source and thereby controlling the amount and rate that fluid is dispensed from the pipe.

Embodiments in accordance with the present invention provide a scrubbing device including a housing and an axle rotatably mounted on the housing. The scrubbing device also includes a motor operatively coupled to the axle. The scrubbing device further includes at least one brush wheel mounted on the axle. The at least one brush wheel includes a plurality of bristles. The scrubbing device also includes a stone wheel mounted on the axle. The scrubbing device further includes a pipe disposed above the axle. The pipe is in fluid communication with a source of fluid. Further, the pipe includes a plurality of holes. In another embodiment of the present invention, a valve may be incorporated into the hand scrubbing device to regulate the flow of fluid from the fluid source, through the pipe and thereby controlling the amount and rate that fluid is dispensed from the pipe.

Embodiments in accordance with the present invention are directed to a scrubbing device including a housing and an axle rotatably mounted on the housing. The scrubbing device includes a motor operatively coupled to the axle. The scrubbing device further includes a first brush wheel mounted on the axle. The first brush wheel includes a plurality of first bristles. The scrubbing device also includes a second brush wheel mounted on the axle adjacent to the first brush wheel. The second brush wheel includes a plurality of second bristles. The scrubbing device further includes a third brush wheel mounted on the axle and spaced apart from the second brush wheel. The third brush wheel includes a plurality of third bristles. The scrubbing device also includes a pumice wheel mounted on the axle between the second brush wheel and the third brush wheel. In other embodiments of the present invention, any number of brush wheels and/or pumice wheels may be placed on the axle in various configurations. The scrubbing device further includes a pipe disposed above the axle. The pipe is in fluid communication with a source of fluid. The pipe includes a plurality of holes. A valve may be incorporated into the hand scrubbing device to regulate the flow of fluid from the fluid source, through the pipe and thereby controlling the amount and rate that fluid is dispensed from the pipe Embodiments in accordance with the present invention are further directed to a scrubbing device including a housing that includes an overspray shield. The scrubbing device also includes an axle rotatably mounted on the housing. The scrubbing device further includes a motor operatively coupled to the axle. The scrubbing device also includes a first brush wheel mounted on the axle. The first brush wheel includes a plurality of first bristles. The first brush wheel has a first width. The scrubbing device further includes a second brush wheel mounted on the axle adjacent to the first brush wheel. The second brush wheel includes a plurality of second bristles. Further, the second brush wheel has a second width equal to the first width. The scrubbing device also includes a third brush wheel mounted on the axle and spaced apart from the second brush wheel. The third brush wheel includes a plurality of third bristles. Further, the third brush wheel has a third width greater than the first width. The scrubbing device further includes a pumice wheel mounted on the axle between the second brush wheel and the third brush wheel. In other embodiments of the present invention, any number of brush wheels and pumice wheels may be placed on the axle in various configurations. The scrubbing device also includes a pipe disposed above the axle. The pipe is in fluid communication with a source of fluid. Further, the pipe includes a plurality of holes. A valve may be incorporated into the hand scrubbing device to regulate the flow of fluid from the fluid source, through the pipe and thereby controlling the amount and rate that fluid is dispensed from the pipe.

Embodiments of the present disclosure may provide a number of advantages depending on its particular configuration. It is an object of the present disclosure to provide a hand scrubbing device, that provides a user a better and an efficient way to clean fingernails, cuticles, hands.

These and other advantages will be apparent from the present application of the embodiments described herein.

The preceding is a simplified summary to provide an understanding of some embodiments of the present disclosure. This summary is neither an extensive nor exhaustive overview of the present disclosure and its various embodiments. The summary presents selected concepts of the embodiments of the present disclosure in a simplified form as an introduction to the more detailed description presented below. As will be appreciated, other embodiments of the present disclosure are possible utilizing, alone or in combination, one or more of the features set forth above or described in detail below.

BRIEF DESCRIPTION OF THE DRAWINGS

The above and still further features and advantages of embodiments of the present disclosure will become apparent upon consideration of the following detailed description of embodiments thereof, especially when taken in conjunction with the accompanying drawings, and wherein.

While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the particular form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present disclosure will be described below in conjunction with exemplary with a scrubbing device. Embodiments of the present disclosure are not limited to any particular position or structure of the scrubbing device. Those skilled in the art will recognize the disclosed application and/or location of the scrubbing device.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

Figure 1:
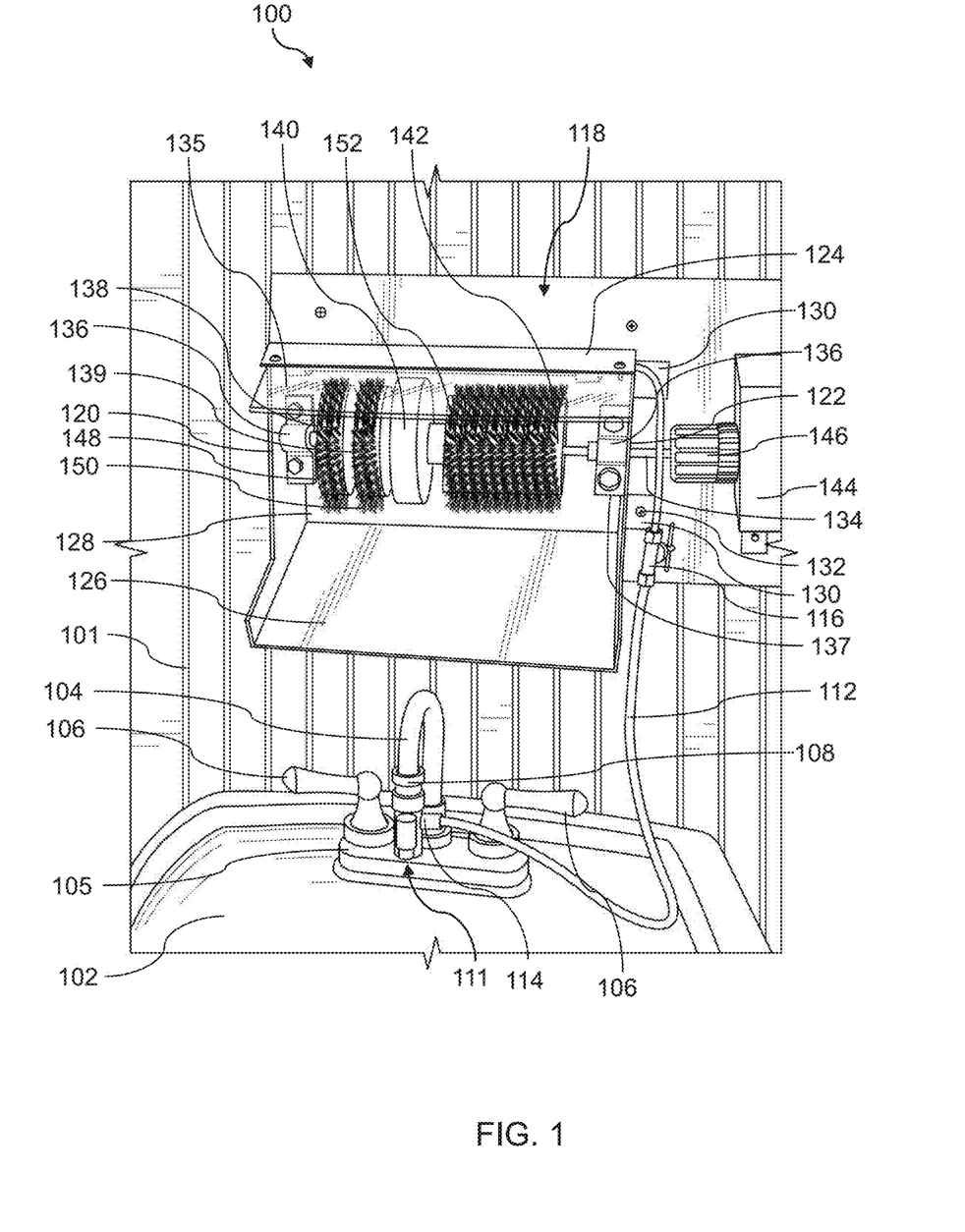
FIG. 1 illustrates a front view of a hand scrubbing device, according to an embodiment of the present disclosure.

FIG. 1 illustrates a front view of a scrubbing device 100, according to an embodiment of the present disclosure. In an exemplary embodiment, the scrubbing device 100 may be a hand scrubbing device. The scrubbing device 100 is mounted above a sink 102 and fixed to a wall 101 by way of screws, bolts or like fasteners. In another embodiment of the present invention, the scrubbing device 100 further comprises a separate mounting kit having a bracket which is mounted to a wall by way of screws, bolts and like fasteners, wherein the scrubbing device 100 is detachably attached to said bracket by way of screws, bolts and like fasteners. In addition, the scrubbing device 100 may be free standing.

The scrubbing device 100 includes a housing 118. The housing 118 is bounded by a first planar surface 120, a second planar surface 122 parallel to the first planar surface 120, a top planar surface 124 extending between the first planar surface 120 and the second planar surface 122, and a bottom planar surface 126 inclined with respect to the top planar surface 124. Further, the bottom planar surface 126 is angled towards the sink 102. The bottom planar surface 126 is inclined for draining fluid from the housing. Specifically, the bottom planar surface 126 may allow residual water to drain into the sink 102, a shower or a drainage hose. In some other embodiments, the bottom planar surface 126 is substantially parallel to the top planar surface 124 and may include a hole (not shown) to allow residual water to drain into the sink 102, a shower or a drainage hose. The housing 118 also includes a third planar surface 128 at the back of the housing 118. In some embodiments, the third planar surface 128 may abut the wall 101. Further, the second planar surface 122 may include a first opening (not shown) for the connection of a tube 112 with the housing 118. The first opening may have a diameter greater than or equal to a diameter of the tube 112 to receive the tube 112 there through. The second planar surface 122 may also include a second opening (not shown) for an axle 134 operatively connected to a power source unit 144. The housing 118 is fixed to the wall 101 via a pair of flanges 130 attached to each of the first planar surface 120 and the second planar surface 122. Each of the pair of flanges 130 may be coupled to the first planar surface 120 and the second planar surface 122 via any mechanical joint, fasteners, and/or adhesive. The pair of flanges 130 allows the fixing of the housing 118 to the wall 101 via screws 132. In an embodiment, each of the flanges 130 may be L-shaped. In alternative embodiments, the housing 118 may be placed on a stand attached to ground. In an exemplary embodiment, the housing 118 may be constructed of injection molded plastic material such as, but not limited to, polyethylene, polypropylene, polystyrene, stainless steel or aluminum.

In an embodiment, the axle 134 may be rotatably mounted on the housing 118. In some embodiments, the axle 134 is detachably mounted on the housing 118. In an exemplary embodiment, the scrubbing device 100 may also include at least one brush wheel mounted on the axle 134. Further, the at least one brush wheel includes a plurality of bristles. In an embodiment, the at least one brush wheel may include a first brush wheel 138, a second brush wheel 139, and a third brush wheel 142 rotatable about an axis "A" (shown in FIG. 4) defined by the axle 134. In some embodiments, the first brush wheel 138 may be mounted on the axle 134. In an embodiment, the first brush wheel 138 includes a plurality of first bristles 148. In some embodiments, the second brush wheel 139 may be mounted on the axle 134 adjacent to the first brush wheel 138. The second brush wheel 139 includes a plurality of second bristles 150. In an embodiment, the third brush wheel 142 may be mounted on the axle 134 and spaced apart from the second brush wheel 139. The third brush wheel 142 may include a plurality of third bristles 152. In some embodiments, the plurality of first, second and third bristles 148, 150, 152 may be uniformly disposed along circumferences of the first brush wheel 138, the second brush wheel 139 and the third brush wheel 142, respectively. In an embodiment, each of the plurality of first, second and third bristles 148, 150, 152 may be arranged in row and column form. In some other embodiments, each of the plurality of first, second and third bristles 148, 150, 152 may be disposed in a zig-zag fashion. In alternative embodiments, each of the plurality of first, second and third bristles 148, 150, 152 may be arranged in a non-uniform fashion. The plurality of first, second and third bristles 148, 150, 152 may be soft bristles, medium bristles, hard bristles or a combination thereof. In some embodiments, a length of each of the plurality of first, second and third bristles 148, 150, 152 may be the same. In some other embodiments, the plurality of first, second and third bristles 148, 150, 152 may have variable lengths. Each of the plurality of first, second and third bristles 148, 150, 152 may include both natural and synthetic materials such as, but not limited to, goat hair, horse hair, camel hair, ox hair along with nylon and synthetic fibers, and so forth. In some other embodiments, each of the plurality of first, second and third bristles 148, 150, 152 may include materials such as, but not limited to, bassine, rice root, union fiber and so forth. The material of each of the first, second and third bristles 148, 150, 152 is so chosen that no harm or physical injury is brought upon the hands of the user.

In an exemplary embodiment, the scrubbing device 100 may also include a stone wheel 140 (interchangeably referred to as "the pumice wheel 140"). In some embodiments, the stone wheel 140 may be a pumice wheel made form pumice rock. In an embodiment, each of the first brush wheel 138, the second brush wheel 139, the stone wheel 140 and the third brush wheel 142 is coupled to the axle 134 to prevent any relative axial and/or rotational movement. Therefore, each of the first brush wheel 138, the second brush wheel 139, the stone wheel 140 and the third brush wheel 142 rotates along with the axle 134. The axle 134 is mounted between the two opposite planar surfaces 120 and 122 of the housing 118. In an exemplary embodiment, the stone wheel 140 is mounted on the axle 134 between the second brush wheel 139 and the third brush wheel 142. Specifically, the stone wheel 140 is axially disposed between the second brush wheel 139 and the third brush wheel 142. In other embodiments, the stone wheel 140 is placed between the first brush wheel 138 and the second brush wheel 139. In yet other embodiments, the first brush wheel 138, the second brush wheel 139 and the third brush wheel 142 are grouped together and the stone wheel 140 is placed at either of the two ends of the axle 134.

The scrubbing device 100 also includes the power source unit 144 operatively connected to the axle 134. Consequently, each of the first brush wheel 138, the second brush wheel 139, the stone wheel 140 and the third brush wheel 142 is rotated by the power source unit 144 via the axle 134. The first brush wheel 138, the second brush wheel 139, the stone wheel 140 and the third brush wheel 142 are at least partially enclosed by the housing 118. The power source unit 144 may be placed near the second planar surface 122. In some other embodiments, the power source unit 144 may be included within the housing 118. The power source unit 144 may include a motor 146 operatively coupled to the axle 134. The motor 146 may include, but not limited to, an electrically excited direct current (DC) motor, a permanent magnet DC motor, a brushless motor and so forth. A shaft of the motor 146 is coupled to the axle 134. Further, the motor 146 may simultaneously rotate each of the of first brush wheel 138, the second brush wheel 139, the stone wheel 140 and the third brush wheel 142. The motor 146 may rotate with a fixed speed. In some other embodiments, the motor 146 may rotate at a variable speed as per requirements. In another embodiment, a regulator (not shown) is provided along with the motor 146 to adjust the speed of the motor 146 accordingly. In yet other embodiments, the motor 146 may be calibrated to a predetermined speed which is suitable for the working of scrubbing device 100. The predetermined speed may be selected so as prevent any possible injury to the hand of the user such as, but not limited to, friction burn.

The power source unit 144 may include a power source, such as a rechargeable battery pack (not shown), configured to supply power to the motor 146. In some embodiments, the rechargeable battery pack may include one or more electrochemical cells. Examples of the rechargeable battery pack may include batteries such as, but not limited to, lead-acid batteries, nickel cadmium (NiCd) batteries, nickel metal hydride (NiMH) batteries, lithium ion (Li-ion) batteries, and lithium ion polymer (Li-ion polymer) batteries and so forth.

In some embodiments, the rechargeable battery pack may be easily removed from the power source unit 144 for charging purposes. In some other embodiments, the power source unit 144 is provided with a power cord (not shown) connected to an internal charger (not shown) to charge the rechargeable battery pack. In yet another embodiment, the power source unit 144 may be provided with a socket (not shown) for a connection to an external charger to charge the rechargeable battery pack. In alternative embodiments, the power source unit 144 may include a primary battery pack to power the motor 146.

In some embodiments, the power source unit 144 is provided with a power cord to plug into a Ground Fault circuit Interrupter (GFI) outlet to supply power to the motor 146. In some other embodiments, the power cord may be plugged into any suitable outlet that supplies sufficient power to run the motor 146.

In some embodiments, the scrubbing device 100 is attached to a water supply, such as a sink, through a tube 112. The sink 102 may include a faucet 104 including a pair of knobs 106 disposed on a body 105 of the faucet 104. Each of the pair of knobs 106 is rotatable to adjust the flow of the water accordingly. In some embodiments, the tube 112, that is configured to dispense water in the housing 118, is attached to a faucet nozzle 108. In some embodiments, the tube 112 may be connected to the faucet nozzle 108 via a tee junction 114. Further, a top opening (not shown) of the tee junction 114 may be connected to the faucet nozzle 108. A central opening (not shown) of the tee junction 114 may be connected to the tube 112, while a bottom opening 111 may be used as an exit of the faucet nozzle 104. Therefore, the pair of knobs 106 may also control the flow of the water in the housing 118. Further, a temperature of the water flowing through the tube 112 is adjusted with the pair of knobs 106, with one of the pair of knobs 106 allowing the outflow of water at a particular temperature and the other knob allowing the outflow of water at a relatively higher temperature. In alternative embodiments, the tube 112 may be connected to the nozzle 108 of the faucet 104 via any joint plugs and/or valves such as, but not limited to, female threaded tees, elbows, crosses and so forth.

In some embodiments, the tube 112 may be connected to the body 105 of the faucet 104 via a pipe fitting such as, but not limited to, a tee, a cross, an elbow and so forth. Further, the flow of water through the tube 112 is controlled via a valve, including but not limited to, a ball valve 116. In other embodiments of the present invention the valve 116 may be placed in any suitable area of the scrubbing device to control the flow of water into and through the scrubbing device. In some embodiments, the ball valve 116 may be a screw ball valve. In some embodiments, the tube 112 may be made of any material such as, but not limited to, metal, rubber, plastic and so forth. Further, the tube 112 may have a flexible structure. In alternative embodiments, the tube 112 may have a rigid structure. Further, the tube 112 may dispense the water in the form of a stream or a spray and may be adjustable in accordance with a user's need. Moreover, the tube 112 may have any suitable shape, size and structure as per requirements. In some embodiments, the tube 112 may include material that can withstand various temperatures of the water. In some other embodiments, the tube 112 may be made of various materials, such as, but not limited to, polyvinyl chloride (PVC), cast iron, copper, steel and so forth.

In some embodiments, the scrubbing device 100 may include a pipe (not shown in FIG. 1) disposed above the axle 134. The pipe is in fluid communication with a source of the fluid, such as the faucet 104. In an exemplary embodiment, the tube 112 is in fluid communication with the pipe. In some embodiments, the scrubbing device 100 may include a reservoir (not shown in FIG. 1) on the top of the housing 118. In an exemplary embodiment, the reservoir may be in fluid communication with the pipe. The reservoir may store a quantity of fluid and/or water for use in the scrubbing device 100. In some embodiments, the reservoir may store a fixed quantity of water wherein the flow of the water into the housing is manually controlled through the use of a valve (not shown) and is gravity dispensed within the housing. In some other embodiments, the reservoir may be connected to a water supply and simultaneously refilled when the water is dispensed through the tube 112. Further, the tube 112 may be directly connected to the reservoir to dispense the water within the housing 118. Alternatively, the reservoir receives water via a tube connected to the tee junction 114. In yet other embodiments, the reservoir may dispense water within the housing 118 through a connecting pipe (not shown in FIG. 1), directly connecting the reservoir with the housing 118. The reservoir may be manufactured from materials such as, but not limited to, polyethylene, fiberglass, steel, aluminum and so forth. In an exemplary embodiment, a material used in the manufacturing of reservoir is same as a material used in manufacturing of the housing 118. A valve (not shown) may be incorporated into the hand scrubbing device to regulate the flow of fluid from the fluid source, thereby controlling the amount and rate that fluid is dispensed into the housing.

The reservoir may be mounted above the scrubbing device 100 and fixed to the wall 101. In some embodiments, the reservoir may be detachably attached to the housing 118 and may be supported by the housing 118 itself. In other embodiments, the reservoir may be fixedly attached to the housing 118. Alternatively, the reservoir may be placed on a stand that is either mounted above the scrubbing device 100 and fixed to the wall 101, or placed on the ground or other suitable area. Alternatively, the reservoir may be attached to the sink 102 and may be supported by the sink 102.

The scrubbing device 100 may also include a soap dispenser (not shown) to dispense soap within the housing 118. In some embodiments, the soap dispenser may be directly connected to the housing 118. In some other embodiments, the soap dispenser may be connected to the housing 118 via a pipe/tube. In alternative embodiments, the soap dispenser may be connected to the housing 118 via the tube 112. The tube 112 may also include one or more control knobs (not shown) to alternatively dispense the soap and the water from the soap dispenser and the reservoir, respectively. In other embodiments, the one or more control knobs may allow simultaneous flow of the water and the soap. Further, the one or more control knobs may control the amount of the soap and/or water flowing through the tube 112. In other embodiments, the reservoir may include two sections, one each for the soap and the water. The soap dispenser may be disposed adjacent to housing 118. The soap dispenser may be provided with a control button, which upon pressing releases soap. The soap dispenser may also be placed on the top of the housing 118. In yet other embodiments, the soap dispenser may automatically dispense the soap along with the water from the reservoir. A valve may be incorporated into the hand scrubbing device to regulate the flow of water and soap from their respective sources, thereby controlling the amount and rate that water and/or soap is dispensed into the housing.

In some embodiments, the reservoir may store an antiseptic or any cleaning agent. Examples of the antiseptic or a composition of the cleaning agent may include, but are not limited to, betaine, chlorhexidine glutamate, iodine, povidone iodine, parachlorometaxylenol, chloroxylenol, triclosan, alcohols, quaternary ammonium compounds, cationic surfactants, anionic surfactants, phenol, polyhexanide, sodium chloride, boric acid, hydrogen peroxide, sodium hypochlorite, terpenes, and mixtures thereof.

In some embodiments, the housing 118 may also include an overspray shield 135 extending along the top planar surface 124 of the housing 118. In some embodiments, the overspray shield 135 is angled downwardly relative to the top planar surface 124. In alternative embodiments, the overspray shield 135 is aligned with the top planar surface 124. The overspray shield 135 may prevent splashing of water on the user while washing. In some embodiments, the overspray shield 135 may contain water or soap or any other cleaning agent used in or near to the scrubbing device 100. The overspray shield 135 may be made of any material, such as, but not limited to, fiberglass, plastic, metal and so forth. In some embodiments, the overspray shield 135 may be integrally manufactured along with the housing 118. In some other embodiments, the overspray shield 135 may be separately manufactured and may be attached to the housing 118 via mechanical joints and/or adhesive. Mechanical joints may include, but not limited to, welding, brazing, nut-bolt joint and so forth.

The scrubbing device 100 includes a pair of bearing joints 136 adjacent to each of the first planar surface 120 and the second planar surface 122 to rotatably support the axle 134 within the housing 118. Supports 137 couple the respective bearing joints 136 to the third planar surface 128. The supports 137 prevent each of the first brush wheel 138, the second brush wheel 139, the stone wheel 140 and the third brush wheel 142 from being in direct contact with the third planar surface 128. The supports 137 may be mechanically coupled to the third planar surface 128. A height of each of the supports 137 may be greater than or equal to the radius of each of the first brush wheel 138, the second brush wheel 139, the stone wheel 140 and the third brush wheel 142. Further, the axle 134 is rotatably mounted on the housing 118 via the bearing joints 136 and the supports 137.

In an embodiment of the present invention, the first brush wheel 138 and the second brush wheel 139 (hereinafter interchangeably referred to as "the wheels 138 and 139") are placed near the first planar surface 120 of the housing 118. In some embodiments, the first brush wheel 138 and the second brush wheel 139 are identical in radius and width. In alternative embodiments, each of the first brush wheel 138 and the second brush wheel 139 may have different radii and widths. In an exemplary embodiment, the first brush wheel 138 and the second brush wheel 139 may provide a better and an efficient cleaning under fingernails, cuticles and so forth. In some other embodiments, the first brush wheel 138 and the second brush wheel 139 may remove deeply embedded dirt and grime and smoothens rough calloused hands.

In some embodiments, the stone wheel 140 is disposed adjacent to the second brush wheel 139. The stone wheel 140 may be manufactured of a synthetic or a natural pumice stone. In some embodiments, the radius of the stone wheel 140 is identical to the radius of each of the first brush wheel 138 and the second brush wheel 139. The stone wheel 140 may be manufactured from a pumice stone. A pumice stone is generally used to smoothen skin. In some other embodiments, the stone wheel 140 may be replaced with alternatives such as, but not limited to, sponges on a wheel. In an exemplary embodiment, the stone wheel 140 may remove deeply embedded dirt and grime and smoothens rough calloused hands. In some embodiments, the stone wheel 140 may provide better and efficient cleaning under fingernails, cuticles and so forth.

The third brush wheel 142 is disposed on the axle 134, adjacent to the stone wheel 140. The width of the third brush wheel may be greater than the width of each of the wheels 138 and 139. In some embodiments, the radius of the third brush wheel 142 is greater than the radius of each of the wheels 138 and 139. The third brush wheel 142 removes deeply embedded dirt and grime and smoothens rough calloused hands. In some embodiments, the third brush wheel 142 may provide a better and an efficient cleaning under fingernails, cuticles and so forth.

In an embodiment, the first brush wheel 138, the second brush wheel 139, the stone wheel 140 and the third brush wheel 142 may allow a user to clean both hands simultaneously. In some embodiments, the user may use the first and second brush wheels 138, 139, and the stone wheel 140 for cleaning one hand, while using the third brush wheel 142 for cleaning another hand simultaneously.

In another embodiment of the present invention, the scrubbing device 100 includes detachable and interchangeable brush and stone wheels of varying sizes, bristle softness, etc. to enable a user to create various combinations of brush wheels, stone wheels, and brush and stone wheels.

In some embodiments, the axle 134 is a spring-loaded axle. Therefore, the axle 134 may allow easy replacement of faulty brush wheels and/or a faulty pumice wheel. The axle 134 allows an easy cleaning of the scrubbing device 100. Specifically, the axle 134 may allow replacement and/or cleaning of the first brush wheel 138, the second brush wheel 139, the stone wheel 140 and the third brush wheel 142. Further, the first brush wheel 138, the second brush wheel 139, the stone wheel 140 and the third brush wheel 142 are attached to the power source unit 144 via the axle 134.

The scrubbing device 100 further includes a control unit (not shown) operatively connected to the power source unit 144. In some embodiments, the control unit may control the speed of the motor 146. In some other embodiments, the control unit may include a regulator for regulating the speed of the motor 146.

In some embodiments, the control unit may include a switch to manually turn off or turn on the motor 146, or the scrubbing device 100. In some other embodiments, the control unit may automatically turn on or turn off the motor 146, or the scrubbing device 100. The control unit may electronically control the flow of water from the reservoir and/or the tube 112. The control unit may also control the flow of the soap in the housing 118 from a soap reservoir.

In some embodiments, the control unit may include various sensors to detect a user such that the scrubbing device 100 is turned on upon detection of the presence of a user and automatically turned off when the presence of the user is not detected. In other embodiment, the control unit may automatically turn off the scrubbing device 100 after a predetermined time duration has elapsed. The various sensors include, but not limited to, ultrasonic sensors, infrared sensors, proximity sensors and so forth. In some other embodiments, the control unit may include a camera to detect the presence of a user. Further, the control unit may be powered by the power source unit 144. In some other embodiments, a sensor unit (not shown) including various sensors is separately placed near to the scrubbing device 100 and may be electrically connected to the control unit. The sensor unit may detect the presence of the user and send a signal to the control unit to turn on or turn off the motor 146. In some embodiments, the control unit may automatically shut down the scrubbing device 100 when too much pressure is applied on any of the first and the second brush wheels 138 and 139, the stone wheel 140 and the third brush wheel 142 by the user to prevent any damage to the user or the scrubbing device 100. In some other embodiments, the control unit may include a separate power supply for various internal components of the control unit. In some embodiments, the control unit may be an integral part of the power source unit 144. In some other embodiments, the control unit may be an integral part of the housing 118.

In an exemplary embodiment, the scrubbing device 100 may be used for hand cleaning. In alternative embodiments, the scrubbing device 100 can used for various applications such as, but not limited to, foot cleaning, and cleaning of other items.

Figure 2:
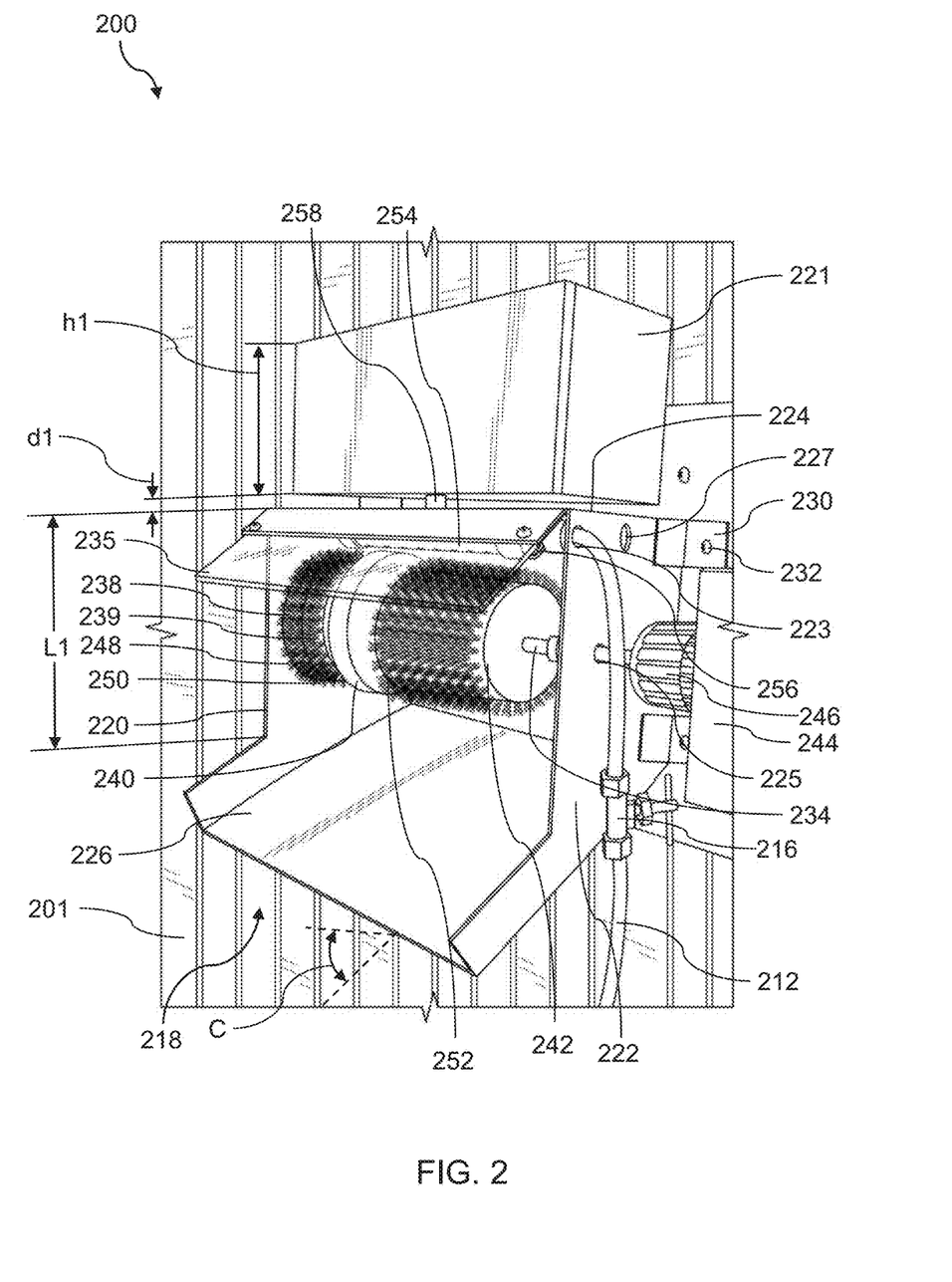
FIG. 2 illustrates a perspective side view of a hand scrubbing device, according to another embodiment of the present disclosure.

FIG. 2 illustrates a perspective side view of a scrubbing device 200 including a reservoir 221. The scrubbing device 200 is mounted above a sink (not shown in FIG. 2) and fixed to a wall 201. The scrubbing device 200 includes a housing 218. The housing 218 at least partially encloses a first brush wheel 238, a second brush wheel 239, a stone wheel 240 and a third brush wheel 242 rotatable about an axis defined by an axle 234. In an embodiment, each of the first brush wheel 238, the second brush wheel 239, the stone wheel 240 and the third brush wheel 242 is coupled to the axle 234 to prevent any relative axial and/or rotational movement. Therefore, each of the first brush wheel 238, the second brush wheel 239, the stone wheel 240 and the third brush wheel 242 rotate along with the axle 234. The axle 234 is mounted at two opposite planar surfaces between longer ends of the housing 218. The stone wheel 240 is placed between the second brush wheel 239 and the third brush wheel 242. In some other embodiments, the stone wheel 240 is placed between the first brush wheel 238 and the second brush wheel 239. In yet other embodiments, the first brush wheel 238, the second brush wheel 239 and the third brush wheel 242 are grouped together and the stone wheel 240 is placed at either of the two ends of the axle 234. The scrubbing device 200 also includes a power source unit 244 operatively connected to the axle 234. Consequently, each of the first brush wheel 238, the second brush wheel 239, the stone wheel 240 and the third brush wheel 242 is rotated by the power source unit 244 via the axle 234. In some embodiments, the scrubbing device 200 is attached to a water supply through a tube 212.

The housing 218 is bounded by a first planar surface 220, a second planar surface 222 parallel to the first planar surface 220, a top planar surface 224 extending between the first planar surface 220 and the second planar surface 222. The housing 218 further includes a bottom planar surface 226 inclined with respect to the top planar surface 224. Specifically, the bottom planar surface 226 may be angled downwardly relative to the top planar surface 224. In an embodiment, the bottom planar surface 226 may be inclined at an angle "C" with respect to the top planar surface 224. The bottom planar surface 226 may allow residual water to drain into a sink, a shower or a drainage hose. In some other embodiments, the bottom planar surface 226 is substantially parallel to the top planar surface 224 and may include a hole (not shown) to allow residual water to drain into a sink, a shower or a drainage hose. The housing 118 also includes a third planar surface (not shown) at the back of the housing 218. In some embodiments, the third planar surface may abut the wall 201. Further, the second planar surface 222 may include a first opening 223 for the connection of the tube 212 with the housing 218. The first opening 223 may have a diameter greater than or equal to a diameter of the tube 212 to receive the tube 212 there through. The second planar surface 222 may also include a second opening 225 for the axle 234 operatively connected to the power source unit 244. The second planar surface 222 also includes a third opening 227 near the top planar surface 224. In some embodiments, the third opening 227 may allow a connection of the housing 218 with a soap dispensing unit. In some other embodiments, the third opening 227 may be provided for a connection of the housing 218 with the reservoir 221. In some embodiments, a length of each of the first planar surface 220 and the second planar surface 222 is "L1". In an exemplary embodiment, the length "L1" is about 6.6 inches.

In alternative embodiments, each of the first planar surface 220 and the second planar surface 222 may have any suitable length as per requirement. The housing 218 is fixed to the wall 201 via a pair of flanges 230 attached to each of the first planar surface 220 and the second planar surface 222. Each of the pair of flanges 230 may be coupled to the first planar surface 220 and the second planar surface 222 via any mechanical joint, fasteners, and/or adhesive. The pair of flanges 230 allows the fixing of the housing 218 to the wall 201 via screws 232. In alternative embodiments, the housing 218 may be placed on a stand attached to ground. In an exemplary embodiment, the housing 218 may be constructed of injection molded plastic material such as, but not limited to, polyethylene, polypropylene, polystyrene or aluminum. The housing 218 may also include an overspray shield 235 extending along the top planar surface 224 of the housing 218. In some embodiments, the overspray shield 235 is angled downwardly relative to the top planar surface 224. The overspray shield 235 may prevent splash of water on the user while washing. In some embodiments, the overspray shield 235 may contain water or soap or any other cleaning agent used in or near to the scrubbing device 200. The overspray shield 235 may be made of any material such as, but not limited to, fiberglass, plastic, metal and so forth. In some embodiments, the overspray shield 235 may be integrally manufactured along with the housing 218. In some other embodiments, the overspray shield 235 may be separately manufactured and may be attached to the housing 218 via mechanical joints and/or adhesive. Mechanical joints may include, but not limited to, welding, brazing, nut-bolt joint and so forth.

In some embodiments, the tube 212 may be connected to a faucet (not shown) via a pipe fitting such as, but not limited to, a tee, a cross, an elbow and so forth. The flow of water through the tube 212 is controlled via a valve, including but not limited to, a ball valve 116. In other embodiments of the present invention the valve 116 may be placed in any suitable area of the scrubbing device to control the flow of water into and through the scrubbing device. In some embodiments, the ball valve 216 may be a screw ball valve. In some embodiments, the tube 212 may be made of any material such as, but not limited to, metal, rubber, plastic and so forth. Further, the tube 212 may have a flexible structure. In alternative embodiments, the tube 212 may have a rigid structure. Further, the tube 212 may dispense the water in the form of a stream or spray and may be adjustable in accordance with a user's need. In some embodiments, the tube 212 may connected to the pipe 254 through a pipe fitting 256. The pipe 254 may be tubular. The pipe fitting 256 may include, but not limited to, tees joints, crosses, double socket joints and so forth. The pipe 254 may be disposed within the housing 218 along the top planar surface 224. Therefore, the pipe 254 is disposed above the axle 234. In some embodiments, the pipe 254 may be mechanically attached to the top planar surface 224. The pipe 254 may include a plurality of holes (not shown) along the length of the pipe 254. The plurality of holes is configured to dispense water or soap uniformly on the first brush wheel 238, the second brush wheel 239, the stone wheel 240 and the third brush wheel 242. In some embodiments, the pipe 254 may dispense water, soap or any other cleansing agent in form of spray or stream. Further, the tube 212 may have any suitable shape, size and structure as per requirements. In some embodiments, the tube 212 may include material that withstands various temperatures of the water. In some other embodiments, the tube 212 may be made of various materials such as, but not limited to, polyvinyl chloride (PVC), cast iron, copper, steel and so forth.

The scrubbing device 200 includes the reservoir 221 on the top of the housing 218. The reservoir 221 may store a quantity of water for use in the scrubbing device 200. In some embodiments, the reservoir 221 may store a fixed quantity of water at a particular time. In some other embodiments, the reservoir 221 may be connected to a water supply and simultaneously refilled during discharge of water through the tube 212. In some embodiments, the reservoir 221 may be filled from the sink or may have a direct feed faucet attachment which is configured to simultaneously refill the reservoir 221 during discharge of water. Further, the tube 212 may be directly connected to the reservoir 221 to dispense the water within the housing 218. In some other embodiments, the reservoir 221 once filled may gravitationally dispense water within the housing 218 through the pipe 254 contained within the housing 218 which evenly disburses the water or liquid contained within the reservoir 221. In some embodiments, the reservoir 221 may be connected to the pipe 254 through some pipe fitting such as, but not limited to, sockets, tees, valves and so forth. In an embodiment, the pipe 254 may be in fluid communication with the reservoir 221 via a connecting pipe 258. The reservoir 221 may be manufactured from materials such as, but not limited to, polyethylene, fiberglass, steel, aluminum and so forth. In an exemplary embodiment, a material used in the manufacturing of the reservoir 221 is same as a material used in manufacturing of the housing 218. In some embodiments, the reservoir 221 may have a height of "h1". In an exemplary embodiment, the height "h1" is about 3.5 inches. Alternatively, the reservoir 221 may have any suitable height as per requirements. In some embodiments, the reservoir 221 and the housing 218 is separated by a distance "d1". The distance "d1" may be about 0.5 inches. In some other embodiments, the reservoir 221 may abut the top planar surface 224 of the housing 218. A valve (not shown) may be incorporated into the hand scrubbing device to regulate the flow of fluid from the reservoir, thereby controlling the amount and rate that fluid is dispensed into the housing.

The reservoir 221 may be mounted above the scrubbing device 200 and fixed to the wall 201. In some embodiments, the reservoir 221 may be detachably attached to the housing 218 and may be supported by the housing 218 itself. In other embodiments, the reservoir 221 may be fixedly attached to the housing 218. Alternatively, the reservoir 221 may be placed on a stand that is either mounted above the scrubbing device 200 and fixed to the wall 201, or placed on ground. Alternatively, the reservoir 221 may be attached to and supported by the sink. A valve (not shown) may be incorporated into the hand scrubbing device to regulate the flow of fluid from the reservoir, thereby controlling the amount and rate that fluid is dispensed from into the housing.

The scrubbing device 200 may also include a soap dispenser (not shown) to dispense soap within the housing 218. In some embodiments, the soap dispenser may be directly connected to the housing 218. In some other embodiments, the soap dispenser may be connected to the housing via a pipe/tube. In alternative embodiments, the soap dispenser may be connected to the housing 218 via the tube 212. In some embodiments, the soap dispenser may dispense soap within the housing 218 through the plurality of holes of the pipe 254 coupled to the top planar surface 224. In some embodiments, the tube 212 may include one or more control knobs (not shown) to alternatively dispense the soap and the water from the soap dispenser and the reservoir 221, respectively. In an alternative embodiment, the one or more control knobs may allow simultaneous flow of the water and the soap. In some embodiments, the one or more control knobs may control the amount of the soap and/or water flowing through the tube 212. In alternative embodiments, the reservoir 221 may include two sections, one each for the soap and the water. In some embodiments, the soap dispenser may be disposed adjacent to housing 118. The soap dispenser may be provided with a control button and a user may use soap from the soap dispenser as per requirements. In some other embodiments, the soap dispenser may be placed on the top of the housing 218. In another embodiment, the soap dispenser may automatically dispense the soap along with the water from the reservoir 221. A valve (not shown) may be incorporated into the hand scrubbing device to regulate the flow of water and/or soap, thereby controlling the amount and rate that water and/or soap is dispensed into the scrubbing device.

In some embodiments, the reservoir 221 may store an antiseptic or any cleaning agent. Example of the antiseptic or a composition of the cleaning agent may include, but not limited to, betaine, chlorhexidine glutamate, iodine, povidone iodine, parachlorometaxylenol, chloroxylenol, triclosan, alcohols, quaternary ammonium compounds, cationic surfactants, anionic surfactants, phenol, polyhexanide, sodium chloride, boric acid, hydrogen peroxide, sodium hypochlorite, terpenes, and mixtures thereof.

The scrubbing device 200 includes a pair of bearing joints (not shown in FIG. 2) adjacent to each of the first planar surface 220 and the second planar surface 222 to rotatably support the axle 234.

The first brush wheel 238 and the second brush wheel 239 (hereinafter interchangeably referred to as "the wheels 238 and 239") are placed near the first planar surface 220 of the housing 218. In an exemplary embodiment, the first brush wheel 238 and the second brush wheel 239 may provide a better and an efficient cleaning under fingernails, cuticles and so forth. In some other embodiments, the first brush wheel 238 and the second brush wheel 239 may remove deeply embedded dirt and grime and smoothens rough calloused hands. The first brush wheel 238 and the second brush wheel 239 include a plurality of first and second bristles 248 and 250 uniformly disposed along each of their respective circumferences. In some embodiments, the first and second bristles 248, 250 are arranged in row and column form. In some other embodiments, the first and second bristles 248, 250 may be disposed in a zig-zag fashion. In alternative embodiments, the first and second bristles 248, 250 are arranged in a non-uniform fashion. The first and second bristles 248, 250 on the wheels 238 and 239 may be soft bristles, medium bristles, hard bristles or a combination thereof. In some embodiments, a length of each of the first and second bristles 248, 250 disposed on the wheels 238 and 239 may be the same. In some other embodiments, the first and second bristles 248, 250 may have variable lengths. The first and second bristles 248, 250 may include materials such as, but not limited to, goat hair, horse hair, camel hair, Ox hair and so forth. In some other embodiments, the first and second bristles 248, 250 may include materials such as, but not limited to, bassine, rice root, union fiber and so forth.

The scrubbing device 200 also includes the stone wheel 240 (interchangeably referred to as "the pumice wheel 240") axially disposed within the housing 218 via the axle 234. The stone wheel 240 is disposed adjacent to the second brush wheel 239. The stone wheel 240 is a synthetic/skin smoothing wheel. The stone wheel 240 may be manufactured from a pumice stone. A pumice stone is generally used to smoothen skin. In some other, the stone wheel 240 may be replaced with alternatives such as, but not limited to, sponges on a wheel. In an exemplary embodiment, the stone wheel 240 may remove deeply embedded dirt and grime and, as a result, smoothens rough calloused hands. In some embodiments, the stone wheel 240 may provide a better and an efficient cleaning under fingernails, cuticles and so forth.

The third brush wheel 242 is disposed on the axle 234, adjacent to the stone wheel 240. Therefore, the stone wheel 240 is mounted on the axle 234 between the second brush wheel 239 and the third brush wheel 242. In an exemplary embodiment, the third brush wheel 242 may include a plurality of third bristles 252 arranged in a uniform fashion along a circumferential area of the third brush wheel 242. In some other embodiments, the third bristles 252 are nonuniformly disposed along the circumferential area of the third brush wheel 242. Further, the third bristles 252 may have a fixed length. In alternative embodiments, the third bristles 252 may have variable length. In an exemplary embodiment, the third brush wheel 242 may remove deeply embedded dirt and grime and smoothens rough calloused hands. In some embodiments, the third brush wheel 242 may provide a better and an efficient cleaning under fingernails, cuticles and so forth. The third bristles 252 disposed on the third brush wheel 242 may include materials such as, but not limited to, goat hair, horse hair, camel hair, Ox hair and so forth. In some other embodiments, the third bristles 252 may include materials such as, but not limited to, bassine, rice root, union fiber and so forth. The material of the third bristles 252 is so chosen that no harm or physical injury is brought upon the hands of the user.

In some embodiments, the axle 234 may be spring-loaded. Therefore, the axle 234 may allow easy removal of each of the first brush wheel 238, the second brush wheel 239, the stone wheel 240 and the third brush wheel 242. The axle 234 further allows an easy cleaning of the scrubbing device 200. Specifically, the axle 234 may allow replacement and/or cleaning of the first brush wheel 238, the second brush wheel 239, the stone wheel 240 and the third brush wheel 242.

Further, the first brush wheel 238, the second brush wheel 239, the stone wheel 240 and the third brush wheel 242 are attached to the power source unit 244 via the axle 134. The power source unit 244 may be placed near to the second planar surface 222. In some other embodiments, the power source unit 244 may be included within the housing 218. In some embodiments, the power source unit 244 may include a motor 246 mechanically coupled to the axle 234. The motor 246 may include, but not limited to, an electrically excited direct current (DC) motor, a permanent magnet DC motor, a brushless motor and so forth. In some embodiments, a shaft of the motor 146 is coupled to the axle 234. Further, the motor 246 may simultaneously rotate each of the of first brush wheel 238, the second brush wheel 239, the stone wheel 240 and the third brush wheel 242. In some embodiments, the motor 246 may rotate with a fixed speed. In some other embodiments, the motor 246 may rotate at a variable speed as per requirements. In another embodiment, a regulator (not shown) is provided along with the motor 246 to adjust the speed of the motor 246 accordingly. In yet other embodiments, the motor 246 may be calibrated to a predetermined speed which is suitable for the working of the scrubbing device 200. The predetermined speed may be selected so as prevent any possible injury to the hand of the user such as, but not limited to, friction burn.

The power source unit 244 may include a rechargeable battery pack (not shown) to power the motor 246. In some embodiments, the rechargeable battery pack may include one or more electrochemical cells. Examples of the rechargeable battery pack may include batteries such as, but not limited to, lead-acid batteries, nickel cadmium (NiCd) batteries, nickel metal hydride (NiMH) batteries, lithium ion (Li-ion) batteries, and lithium ion polymer (Li-ion polymer) batteries and so forth. In some embodiments, the rechargeable battery pack may be easily removed from the power source unit 244 for charging purposes. In some other embodiments, the power source unit 244 is provided with a power cord connected to an internal charger (not shown) to charge the rechargeable battery pack. In yet another embodiment, the power source unit 244 may be provided with a socket (not shown) for a connection to an external charger to charge the rechargeable battery pack. In alternative embodiments, the power source unit 244 may include a primary battery pack to power the motor 246.

In some embodiments, the power source unit 244 is provided with a power cord to plug into a Ground Fault circuit Interrupter (GFI) outlet to supply power to the motor 246. In some other embodiments, the power cord may be plugged into any suitable outlet that supplies sufficient power to run the motor 246.

The scrubbing device 200 further includes a control unit (not shown) operatively connected to the power source unit 244. In some embodiments, the control unit may control the speed of the motor 246. In some other embodiments, the control unit may include the regulator configured to regulate the speed of the motor 246.

In some embodiments, the control unit may include a switch to manually turn off or turn on the motor 246, or the scrubbing device 200. In some other embodiments, the control unit may automatically turn on or turn off the motor 246, or the scrubbing device 200. The control unit may electronically control the flow of water from the reservoir 221 and/or tube 212. The control unit may also control the flow of the soap in the housing 218 from the soap reservoir.

In some embodiments, the control unit may include various sensors to detect a user such that the scrubbing device 200 is turned on upon detection of the presence of a user and automatically turned off when the presence of the user is not detected. In other embodiment, the control unit may automatically turn off the scrubbing device 200 after a predetermined time duration has elapsed. The various sensors include to, but not limited to, ultrasonic sensors, infrared sensors, proximity sensors and so forth. In some other embodiments, the control unit may include a camera to detect the presence of the user. Further, the control unit may be powered by the power source unit 244. In some other embodiments, a sensor unit (not shown) including various sensors is separately placed near the scrubbing device 200 and may be electrically connected to the control unit. The sensor unit may detect the presence of a user and send a signal to the control unit to turn on or turn off the motor 246. In some embodiments, the control unit may automatically shut down the scrubbing device 200 when too much pressure is applied on any of the first and the second brush wheels 238 and 239, the stone wheel 240 and the third brush wheel 242 by the user to prevent any damage to the user or the scrubbing device 200. In some other embodiments, the control unit may include a separate power supply for various internal components of the control unit. In some embodiments, the control unit may be an integral part of the power source unit 244. In some other embodiments, the control unit may be an integral part of the housing 218.

In some embodiments, the scrubbing device 200 may also include an ultra violet (UV) light source (not shown) for killing bacteria on the user's hands. The UV light source may be positioned within the housing 218 such that it covers a maximum possible area around the wheels 238, 239, 240 and 242. The UV light source may be powered by the power source unit 244. The UV light source may emit an electromagnetic radiation with a wavelength from 10 nm to 400 nm. In some other embodiments, the UV light source may kill bacteria present on the first and the second brush wheels 238 and 239, the stone wheel 240 and the third brush wheel 242.

Figure 3:
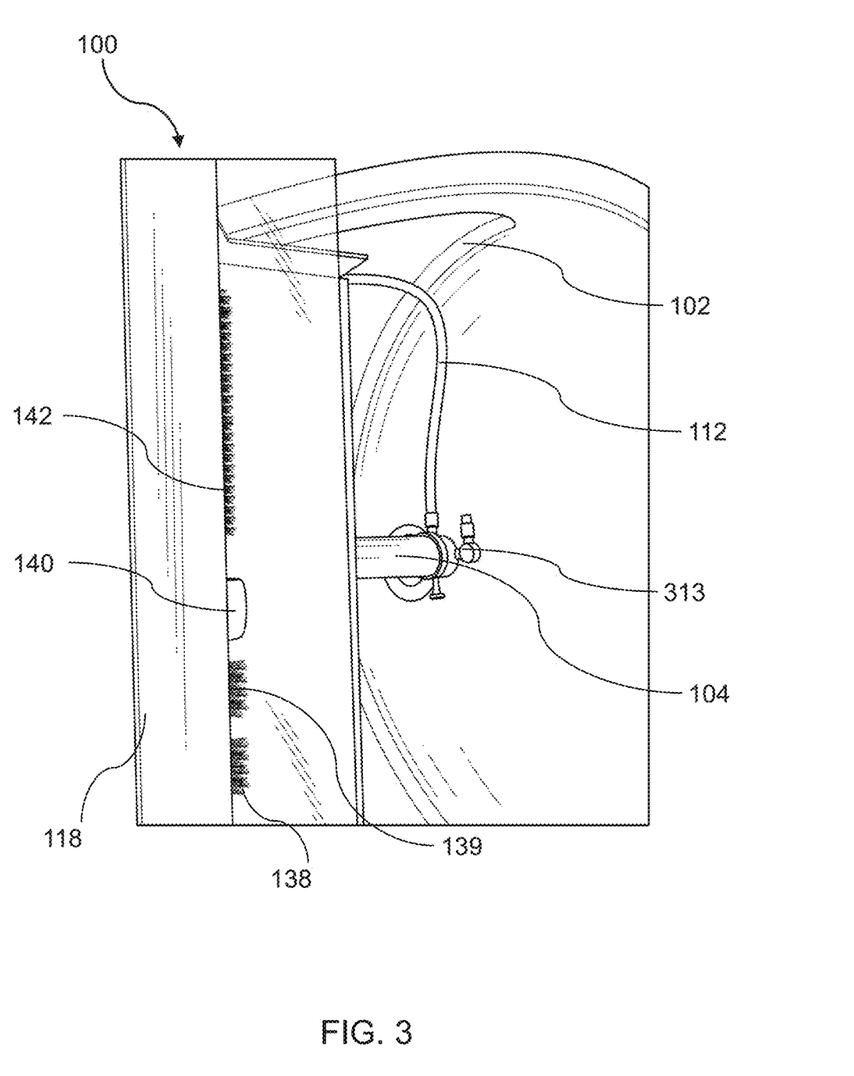
FIG. 3 illustrates a top view of the hand scrubbing device of FIG. 1.

FIG. 3 illustrates a top view of the scrubbing device 100. The scrubbing device 100 is mounted above the sink 102. Referring to FIGS. 1 and 3, the scrubbing device 100 includes the housing 118 at least partially enclosing the first brush wheel 138, the second brush wheel 139, the stone wheel 140 and the third brush wheel 142 rotatable about the axis "A" (shown in FIG. 4).

The sink 102 may include the faucet 104 including the pair of knobs 106 disposed on the body 105 of the faucet 104. The flow of water to the nozzle 108 is controlled via the pair of knobs 106. In some embodiments, the tube 112, that is configured to dispense water in the housing 118, is attached to the nozzle 108. In some embodiments, the tube 112 may be connected to the nozzle 108 via a pipe fitting 109, such as, but not limited to, a tee junction, a cross junction, a valve and so forth. Therefore, the pair of knobs 106 may also control the flow of the water in the housing 118 of the scrubbing device 100. Further, the temperature of the water flowing through the tube 112 is easily adjusted with the pair of knobs 106. In some embodiments, the pipe fitting 109 includes a control valve 313. The control valve 313 may also control the flow of the water through the tube 112. In alternative embodiments, the tube 112 may be connected to the nozzle 108 of the faucet 104 via any joint plugs and/or valves such as, but not limited to, female threaded tees, elbows, crosses and so forth. In other embodiments of the present invention, a valve (not shown) may be incorporated into the hand scrubbing device to regulate the flow of fluid from the fluid source thereby controlling the amount and rate that fluid is dispensed into the housing.

Figure 4:
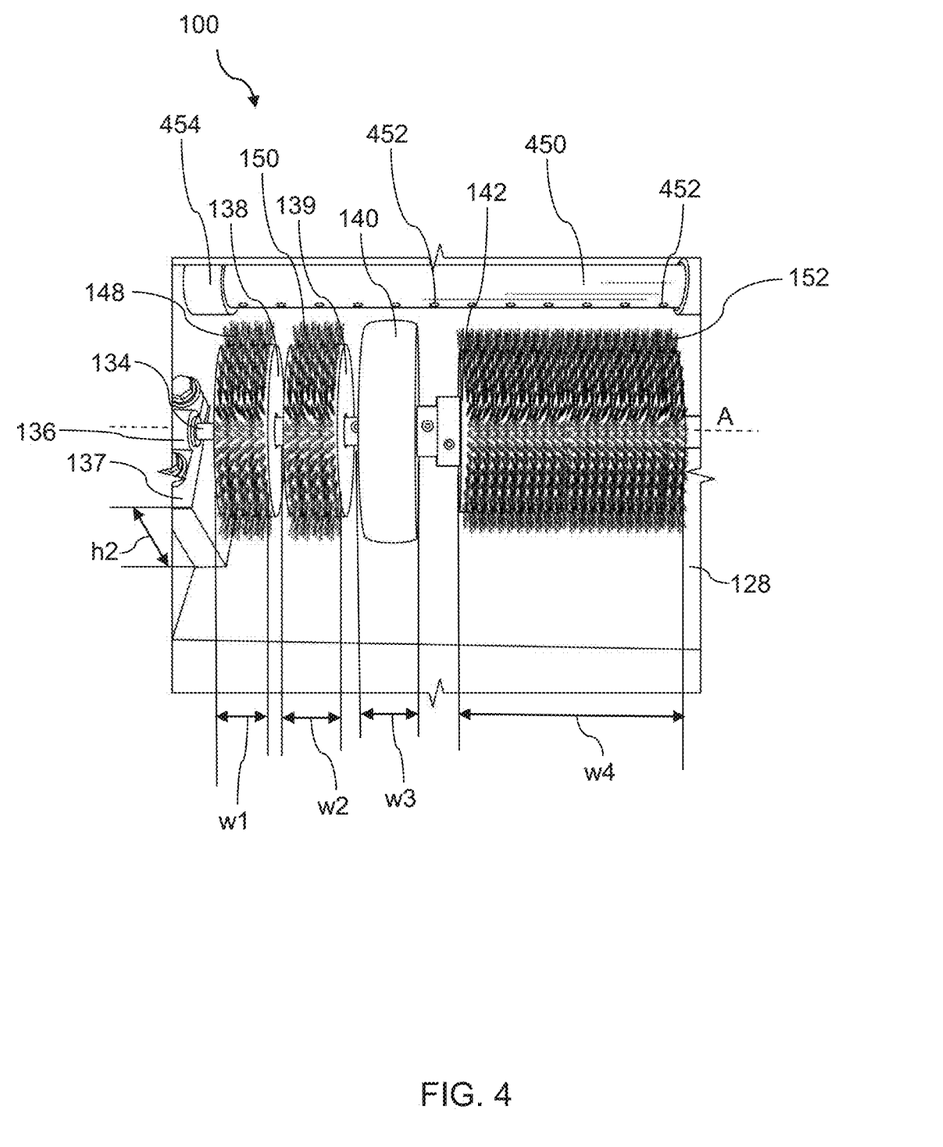
FIG. 4 illustrates a bottom view of the hand scrubbing device of FIG. 1.

FIG. 4 illustrates a bottom view of the scrubbing device 100. Referring to FIGS. 1 and 4, the scrubbing device 100 is mounted above the sink 102. The scrubbing device 100 includes the housing 118 at least partially enclosing the first brush wheel 138, the second brush wheel 139, the stone wheel 140 and the third brush wheel 142 rotatable about the axis "A" defined by the axle 134. The stone wheel 140 is placed between the second brush wheel 139 and the third brush wheel 142. In some embodiments, the stone wheel 140 is placed between the first brush wheel 138 and the second brush wheel 139. In yet other embodiments, the first brush wheel 138, the second brush wheel 139 and the third brush wheel 142 are grouped together and the stone wheel 140 is placed at either of the two ends of the axle 134. In some embodiments, the scrubbing device 100 is attached to a water supply through the tube 112. In other embodiments of the present invention, the water source for the scrubbing device 100 may be a reservoir. In yet another embodiment of the present invention, the scrubbing device 100 includes multiple detachable and interchangeable brush and stone wheels of varying sizes, bristle softness, etc. to enable a user to create various combinations of brush wheels, stone wheels and brush and pumice wheels.

The housing 118 is bounded by the first planar surface 120, the second planar surface 122 parallel to the first planar surface 120, the top planar surface 124 extending between the first planar surface 120 and the second planar surface 122, and the bottom planar surface 126 angled towards the sink 102 relative to the top planar surface 124. The bottom planar surface 126 may allow residual water to drain into the sink 102, a shower or a drainage hose. In some other embodiments, the bottom planar surface 126 is substantially parallel to the top planar surface 124 and may include a hole to allow residual water to drain into the sink 102, a shower or a drainage hose. The housing 118 also includes the third planar surface 128 at the back of the housing 118.

The scrubbing device 100 includes the one or more bearing joints 136 adjacent to each of the first planar surface 120 and the second planar surface 122 to rotatably support the axle 134 within the housing 118. Each of the bearing joints 136 may include the support 137 between the third planar surface 128 and the bearing joints 136. Each of the supports 137 prevent each of the first brush wheel 138, the second brush wheel 139, the stone wheel 140 and the third brush wheel 142 from being in direct contact with the third planar surface 128. The supports 137 may be mechanically coupled to the third planar surface 128. A height "h2" of each of the supports 137 may be greater than or equal to the radii of each of the first brush wheel 138, the second brush wheel 139, the stone wheel 140 and the third brush wheel 142.

The first brush wheel 138 and the second brush wheel 139 are placed near the first planar surface 120 of the housing 118. In some embodiments, the first brush wheel 138 and the second brush wheel 139 are identical in radius. The first brush wheel 138 may have a first width "w1". The second brush wheel 139 may have a second width "w2". In some embodiments, the second width "w2" is equal to the first width "w1". In alternative embodiments, each of the first brush wheel 138 and the second brush wheel 139 may have different radii and widths. In an exemplary embodiment, the first brush wheel 138 and the second brush wheel 139 may provide a better and an efficient cleaning under fingernails, cuticles and so forth. In some other embodiments, the first brush wheel 138 and the second brush wheel 139 may remove deeply embedded dirt and grime and smoothens rough calloused hands. In an embodiment, the first brush wheel 138 and the second brush wheel 139 include the first and second bristles 148, 150 uniformly disposed along each of their respective circumferences. In some embodiments, each of the first and second bristles 148, 150 are arranged in row and column form. In some other embodiments, the first and second bristles 148, 150 may be disposed in a zig-zag fashion. In alternative embodiments, the first and second bristles 148, 150 are arranged in a non-uniform fashion. The first and second bristles 148, 150 on the first and second brush wheels 138 and 139, respectively, may be soft bristles, medium bristles, hard bristles or a combination thereof. In some embodiments, the length of each of the first and second bristles 148, 150 may be the same. In some other embodiments, the first and second bristles 148, 150 may have variable lengths. The first and second bristles 148, 150 may include materials such as, but not limited to, goat hair, horse hair, camel hair, ox hair and so forth. In some other embodiments, the first and second bristles 148, 150 may include materials such as, but not limited to, bassine, rice root, union fiber and so forth.

The scrubbing device 100 also includes the stone wheel 140 axially disposed within the housing 118 via the axle 134. The stone wheel 140 is disposed adjacent to the first brush wheel 138 and the second brush wheel 139. The stone wheel 140 may be manufactured of a synthetic or a natural pumice stone. In some embodiments, a radius of the stone wheel 140 is identical to the radius of each of the first brush wheel 138 and the second brush wheel 139. The stone wheel 140 may be manufactured from a pumice stone. A pumice stone is generally used to smoothen skin. The stone wheel 140 may have a width "w3". In some embodiments, the widths "w3", "w1" and "w2" are identical. In some other embodiments, the stone wheel 140 may be replaced with alternatives such as, but not limited to, sponges on a wheel. In an exemplary embodiment, the stone wheel 140 may remove deeply embedded dirt and grime and smoothens rough calloused hands. In some embodiments, the stone wheel 140 may provide better and efficient cleaning under fingernails, cuticles and so forth.

The third brush wheel 142 is disposed on the axle 134, adjacent to the stone wheel 140. The width of the third brush wheel is greater than the width of each of the wheels 138 and 139. In some embodiments, the radius of the third brush wheel 142 is greater than the radius of each of the wheels 138 and 139. The third brush wheel 142 may have a third width "w4". In an exemplary embodiment, the third width "w4" is greater than each of the widths "w1', w2" and "w3". Specifically, the third width "w4" of the third brush wheel 142 is greater than the first width "w1" of the first brush wheel 138. Further, the third width "w4" may be selected so as to provide a better surface area for bristles to clean the user's hand properly. In an exemplary embodiment, the third brush wheel 142 may include the third bristles 152 arranged in a uniform fashion along a circumferential area of the third brush wheel 142. In some other embodiments, the third bristles 152 are non-uniformly disposed along the circumferential area of the third brush wheel 142. Further, the third bristles 152 may have a fixed length. In other embodiments, the third bristles 152 may have variable length. The third brush wheel 142 may remove deeply embedded dirt and grime and smoothens rough calloused hands.

The third brush wheel 142 may provide a better and an efficient cleaning under fingernails, cuticles and so forth. The third bristles 152 disposed on the third brush wheel 142 may include materials such as, but not limited to, goat hair, horse hair, camel hair, ox hair and so forth. In some other embodiments, the third bristles 152 may include materials such as, but not limited to, bassine, rice root, union fiber and so forth. The material of the third bristles 152 is so chosen that no harm or physical injury is brought upon the hands of the user.

In an embodiment, the arrangement and dimensions of the first brush wheel 138, the second brush wheel 139, the stone wheel 140 and the third brush wheel 142 may allow a user to clean both hands simultaneously. In some embodiments, the user may use the first and second brush wheels 138, 139, and the stone wheel 140 for cleaning one hand, while using the third brush wheel 142 for cleaning another hand simultaneously.

In some embodiments, the axle 134 is a spring-loaded axle. In some embodiments, the axle 134 includes springs (not shown) at each end of the axle. The springs may be coupled to the bearing joints 136. The springs may allow easy removal of the axle 134 from the bearing joints 136. Further, the axle 134 may allow easily removal of each of the first brush wheel 138, the second brush wheel 139, the stone wheel 140 and the third brush wheel 142. The axle 134 further allows an easy cleaning of the scrubbing device 100. Specifically, the axle 134 may allow replacement and/or cleaning of the first brush wheel 138, the second brush wheel 139, the stone wheel 140 and the third brush wheel 142. In an embodiment, the axle 134 may be a hollow cylindrical shaft. In another embodiment, the axle 134 may be a solid cylindrical shaft.

In some embodiments, the scrubbing device 100 includes a pipe 450 connected to a reservoir or a water supply. The pipe 450 is disposed above the axle 134. Further, the pipe 450 is in fluid communication with a source of fluid, such as the faucet 104. The pipe 450 may be disposed along the top planar surface 124. In some embodiments, the pipe 450 may be mechanically attached to the top planar surface 124. The pipe 450 may include a plurality of holes 452 along the length of the pipe 450. The plurality of holes 452 is configured to dispense water, soap or any other cleansing agent uniformly on the first brush wheel 138, the second brush wheel 139, the stone wheel 140 and the third brush wheel 142. In some embodiments, the pipe 450 may dispense water, soap or any other cleansing agent in form of a spray or a stream. The pipe 450 may be made of materials such as, but not limited to, polyvinyl chloride, plastic, metal, and so forth. The pipe 450 may be coupled to the reservoir 221 (shown in FIG. 2) via seal joints 454. In some embodiments, the seal joints 454 may connect the pipe 450 to the tube 112. A valve (not shown) may be incorporated into the hand scrubbing device to regulate the flow of fluid from the fluid source, through the pipe 450 and thereby controlling the amount and rate that fluid is dispensed from the pipe 450 into the housing 118.

Although the disclosure has been described with reference to exemplary embodiments, it is not limited thereto. Those skilled in the art will appreciate that numerous changes and modifications may be made to the preferred embodiments of the disclosure and that such changes and modifications may be made without departing from the true spirit of the disclosure. It is therefore intended that the appended claims be construed to cover all such equivalent variations as fall within the true spirit and scope of the disclosure.

The exemplary embodiments of this present disclosure have been described in relation to fence assemblies. However, to avoid unnecessarily obscuring the present disclosure, the preceding description omits a number of known structures and devices. This omission is not to be construed as a limitation of the scope of the present disclosure. Specific details are set forth by use of the embodiments to provide an understanding of the present disclosure. It should however be appreciated that the present disclosure may be practiced in a variety of ways beyond the specific embodiments set forth herein.

A number of variations and modifications of the present disclosure can be used. It would be possible to provide for some features of the present disclosure without providing others.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present disclosure has been presented for purposes of illustration and description. It is not intended to limit the present disclosure to the form or forms disclosed herein. In the foregoing Detailed Description, for example, various features of the present disclosure are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention the present disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present disclosure.

Moreover, though the description of the present disclosure has included description of one or more embodiments, configurations, or aspects and certain variations and modifications, other variations, combinations, and modifications are within the scope of the present disclosure, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A scrubbing device comprising:
a housing;
an axle rotatably mounted on the housing;
a motor operatively coupled to the axle;
a first brush wheel mounted on the axle, the first brush wheel having a plurality of first bristles, wherein the first brush wheel has a first width;
a second brush wheel mounted on the axle adjacent to the first brush wheel, the second brush wheel having a plurality of second bristles, wherein the second brush wheel has a second width equal to the first width;
a third brush wheel mounted on the axle and spaced apart from the second brush wheel, the third brush wheel having a plurality of third bristles, wherein the third brush wheel has a third width greater than the first width, and wherein the stone wheel is mounted on the axle between the second brush wheel and the third brush wheel;
a stone wheel mounted on the axle; and
a pipe having a plurality of holes, wherein the pipe is disposed above the axle and is in fluid communication with a source of fluid.

2. The scrubbing device of claim 1, wherein the axle is detachably mounted on the housing.

3. The scrubbing device of claim 1, wherein the housing further comprises an overspray shield.

4. The scrubbing device of claim 1, further comprising a reservoir in fluid communication with the pipe.

5. The scrubbing device of claim 1, further comprising a battery configured to supply power to the motor.

6. The scrubbing device of claim 1, wherein the housing comprises a bottom planar surface which is inclined for draining fluid from the housing.

7. The scrubbing device of claim 1, further comprising a valve to regulate the flow of fluid through the scrubbing device.

8. The scrubbing device of claim 1, wherein the stone wheel is a pumice wheel.

9. A scrubbing device comprising:
a housing;
an axle rotatably mounted on the housing;
a motor operatively coupled to the axle;
a first brush wheel mounted on the axle, the first brush wheel having a plurality of first bristles;
a second brush wheel mounted on the axle adjacent to the first brush wheel, the second brush wheel having a plurality of second bristles;
a third brush wheel mounted on the axle and spaced apart from the second brush wheel, the third brush wheel having a plurality of third bristles;
a pumice wheel mounted on the axle between the second brush wheel and the third brush wheel; and
a pipe having a plurality of holes, wherein the pipe is disposed above the axle and is in fluid communication with a source of fluid.

10. The scrubbing device of claim 9, wherein:
the first brush wheel has a first width,
the second brush wheel has a second width equal to the first width; and
the third brush wheel has a third width greater than the first width.

11. The scrubbing device of claim 9, wherein the axle is detachably mounted on the housing.

12. The scrubbing device of claim 9, wherein the housing further comprises an overspray shield.

13. The scrubbing device of claim 9, further comprising a reservoir in fluid communication with the pipe.

14. The scrubbing device of claim 9, further comprising a battery configured to supply power to the motor.

15. The scrubbing device of claim 9, wherein the housing comprises a bottom planar surface which is inclined for draining fluid from the housing.

16. The scrubbing device of claim 9, further comprising a valve to regulate the flow of fluid through the scrubbing device.

17. A scrubbing device comprising:
a housing including an overspray shield;
an axle rotatably mounted on the housing;
a motor operatively coupled to the axle;
a first brush wheel mounted on the axle, the first brush wheel having a plurality of first bristles, wherein the first brush wheel has a first width;
a second brush wheel mounted on the axle adjacent to the first brush wheel, the second brush wheel having a plurality of second bristles, wherein the second brush wheel has a second width equal to the first width;
a third brush wheel mounted on the axle and spaced apart from the second brush wheel, the third brush wheel having a plurality of third bristles, wherein the third brush wheel has a third width greater than the first width;
a pumice wheel mounted on the axle between the second brush wheel and the third brush wheel; and
a pipe having a plurality of holes, wherein the pipe is disposed above the axle and is in fluid communication with a source of fluid.

18. The scrubbing device of claim 17, further comprising a reservoir in fluid communication with the pipe.

19. The scrubbing device of claim 17, further comprising a battery configured to supply power to the motor.

* * * * *